(12) United States Patent
Halaka (10) Patent No.: US 9,587,236 B2
(45) Date of Patent: Mar. 7, 2017

(54) CONTINUOUS SONICATION FOR BIOTECHNOLOGY APPLICATIONS AND BIOFUEL PRODUCTION

(71) Applicant: Folim G. Halaka, Lake Forest, IL (US)

(72) Inventor: Folim G. Halaka, Lake Forest, IL (US)

( * ) Notice: Subject to any disclaimer, the term of this patent is extended or adjusted under 35 U.S.C. 154(b) by 0 days.

(21) Appl. No.: 13/744,819

(22) Filed: Jan. 18, 2013

(65) Prior Publication Data

US 2014/0206060 A1    Jul. 24, 2014

(51) Int. Cl.
  *C12N 13/00*    (2006.01)
  *C12N 1/06*     (2006.01)
  *C12M 1/33*     (2006.01)

(52) U.S. Cl.
  CPC ............. *C12N 13/00* (2013.01); *C12M 45/02* (2013.01); *C12N 1/066* (2013.01)

(58) Field of Classification Search
  CPC .. C12N 13/00; B01J 19/10; B01J 2219/00486
  USPC ................... 435/173.7, 306.1; 422/544, 551; 310/322, 334, 369
  See application file for complete search history.

(56) References Cited

U.S. PATENT DOCUMENTS

| | | | |
|---|---|---|---|
| 3,269,172 A * | 8/1966 | McGaughey | ................. 324/71.4 |
| 4,697,751 A | 10/1987 | Chiba | |
| 4,874,137 A | 10/1989 | Chiba | |
| 4,914,966 A | 4/1990 | White, Jr. | |
| 4,983,523 A | 1/1991 | Li et al. | |
| 5,026,167 A * | 6/1991 | Berliner, III. | ......... B01F 5/0268 |
| | | | 261/DIG. 48 |
| 5,074,474 A | 12/1991 | Bolz et al. | |
| 5,538,628 A * | 7/1996 | Logan | .................... B01D 17/04 |
| | | | 210/198.1 |
| 6,016,023 A | 1/2000 | Nilsson et al. | |
| 6,071,480 A * | 6/2000 | Halaka | .......................... 422/128 |

(Continued)

FOREIGN PATENT DOCUMENTS

KR    10-2012-0017038    2/2012

OTHER PUBLICATIONS

International Search Report and Opinion May 23, 2014.
PCT International Preliminary Report on Patentability, PCT/US14/11801, Jul. 30, 2015.

*Primary Examiner* — William H Beisner
*Assistant Examiner* — Danielle Henkel
(74) *Attorney, Agent, or Firm* — Clifford H. Kraft (57) ABSTRACT

A system and method for sonication of multiple samples and continuous sonication of an input fluid stream in flow-through arrangements useful for economical breakdown of particulates and organisms present in large volumes with relatively low-power sonication devices such as production of oil from algae. The system includes an electrical wave generator oscillating in the ultrasound range, a vibrating element electrically connected to the electrical wave generator, and a sonication plate that vibrates in certain modes. The sonication plate contains features for mating with sample tubes, and the sample tubes also possess complimentary mating features to those on the sonication plate. A method for sonication of multiple samples includes utilizing mating features to attach tubes to the sonication plate and energizing the sonicator to vibrate the sonication plate. The invention also relates to arrangements for continuous flow-through useful for sonicating large sample volumes.

15 Claims, 8 Drawing Sheets

(56) References Cited

U.S. PATENT DOCUMENTS

| | | |
|---|---|---|
| 6,686,195 B1 | 2/2004 | Colin et al. |
| 6,939,696 B1 | 9/2005 | Llorin et al. |
| 7,004,282 B2 | 2/2006 | Manna et al. |
| 7,541,166 B2 | 6/2009 | Belgrader et al. |
| 7,785,868 B2 | 8/2010 | Yuan |
| 7,785,869 B2 | 8/2010 | Belgrader et al. |
| 8,169,122 B1 | 5/2012 | Roberts |
| 2002/0197282 A1* | 12/2002 | Mohseni et al. .............. 424/400 |
| 2011/0151577 A1 | 6/2011 | Zhang et al. |
| 2013/0164754 A1* | 6/2013 | Malik et al. ................. 435/6.12 |

* cited by examiner

Figure 1

SECTION A- - -A
of FIG. 1

DETAIL C

CONTINUOUS SONICATION FOR BIOTECHNOLOGY APPLICATIONS AND BIOFUEL PRODUCTION

FIELD OF THE INVENTION

The present invention relates to non-invasive sonication of multiple samples and to the continuous sonication of effluent streams in flow-through arrangements using optimized coupling of vibrating elements and the sample containers.

BACKGROUND AND PRIOR ART

The present invention describes a sonication device for the breakage of the constituents present in a liquid sample. The invention addresses multiple samples and continuous sonication of an input fluid stream in flow-through arrangements, particularly useful for economical breakdown of organisms in large volumes.

By sonication, it is meant applying mechanical vibration energy at particular frequency to a sample. The sample is generally a liquid containing suspended items of interest. The vibration frequencies are generally in the ultrasonic range. Ultrasonic energy is transmitted in a medium through wave propagation which causes pressure changes within the medium. Suspended items which are unable to withstand the pressure changes are disrupted.

"Sonicators" are generally constructed from an electrical power supply, power control circuitry, vibrating elements, and implements coupled to the vibrating element, which delivers energy to intended samples. Examples are described in my U.S. Pat. No. 6,071,480. The electrical power supply and electronics provides controllable oscillating energy in the ultrasonic frequency range. The vibrating element is a transducer or an actuator, typically a substance that converts electrical energy into mechanical vibrations. The vibrational energy is transferred to vibratable elements such as a probe (probe sonicators), liquid container (bath sonicators), or a horn. A converter is sometimes inserted between the vibratable element and the transducer, for the purpose of modifying the energy density. Piezoelectric transducers, such as piezoelectric crystals or ceramics, are generally used as vibrating elements and are extensively studied in the art to convert electrical energy into mechanical energy. Multiple transducers can be stacked, and several such configurations are also known in the art. The vibratable element is coupled to the transducer and acts as a conveyer to deliver the vibrational energy, optionally through other end-use implements, to the intended sample.

By coupling, it is meant the interface between two distinct components. In ultrasonic devices, coupling is applied to reduce the energy loss as the vibrational energy moves across distinct component interfaces. Coupling typically attempts to match, or minimize the difference between, the acoustic impedance of disparate interacting components.

Sonication energy is utilized in a wide variety of industrial and biological applications. For biological samples, applications include lysis, or breakage, of biological microorganisms, including bacteria, viruses, spores, plant cells, etc.

In applying to biological material, sonication devices (sonicators) most commonly used are bath sonicators, in which an ultrasonic device energizes water in a bath. Tubes containing samples to be sonicated are placed in the bath. The ultra-sonic waves produced by the sonication device transfer into the bath liquid and further to the sample tubes to break the organisms therein. U.S. Pat. Nos. 4,874,137, and 6,939,696 disclose arrangements of bath sonicators. Bath sonicator arrangements generally suffer from inefficient utilization of provided energy. U.S. Pat. No. 4,697,751 describes an ultrasonic disintegrating apparatus with a tank containing a liquid and with an ultrasonic wave generator means coupled to a bottom wall of said tank.

The invention also describes arrangements for continuous flow-through useful for large sample volumes. These arrangements allow the use of relatively low power sonication energy to affect large sample volumes, and overcome some of the limitations present in prior art.

U.S. Pat. No. 7,785,869 and similarly U.S. Pat. No. 7,541,166, describe sonication to selectively lyse different cell types using different sonication energy and using microfluidic circuitry for moving fluids.

U.S. Pat. No. 6,016,023 describes a tubular ultrasonic transducer with a gas cooling features to cool the transducer.

U.S. Pat. No. 5,074,474 describes an arrangement which includes the direct immersion of the tip, or horn, of the sonication device into the sample. While this arrangement provides an efficient utilization of energy, it suffers from cross contamination issues and more complicated workflow.

U.S. Pat. No. 4,983,523 describes an arrangement where ultrasonic energy is directly applied to (the outside of) a vessel containing a sample.

U.S. Pat. No. 7,004,282 describes an ultrasonic horn to provide an ultrasonic device that could treat a full microtiter tray, with the ultrasonic horn having a plurality of fingers disposed in a rectangular array for that purpose.

U.S. Pat. No. 6,686,195 describes method and apparatus for ultrasonic lysis of biological cells, where a "sonotrode" provides ultrasound of variable power to a sample receptacle where the bottom of the sample receptacle is in direct contact with the sonotrode. The sample receptacles were kept in place by variable weight forces on top of each tube to minimize lysis variability.

My U.S. Pat. No. 6,071,480 describes a sonicator having an electrical wave generator, a vibrating element electrically connected to the electrical wave generator and a vibratable member transversely secured to the vibrating element. The sonicator can be employed to sonicate a test sample by generating a standing sonic wave across a vibratable member. U.S. Pat. No. 6,071,480 provides the sonication of discrete test samples, but does not disclose arrangements or methods applicable to continuous sonication applicable to large volumes. Although methods of modifying the holes in the plates using, e.g. threads, are mentioned in U.S. Pat. No. 6,071,480, no description of the tube attachment features to optimize the vibrational coupling of the tubes to the plate is detailed. Additionally, the attachment of the sample tube to the plate is operator-dependent in that the torque applied is not calibrated and as such is subject to the operator judgment and physical strength.

SUMMARY OF THE INVENTION

The present invention relates to sonication of multiple samples and continuous sonication of an input fluid stream in flow-through arrangements. The invention is particularly useful for economical breakdown of particulates and organisms present in large volumes with relatively low-power sonication devices. Production of oil from algae is an example. In one embodiment, a sonication device is described which contains an electrical wave generator oscillating in the ultrasound range, a vibrating element electrically connected to the electrical wave generator, and a sonication plate that vibrates in certain modes. The sonication plate contains features for mating with sample tubes, and the sample tubes also possess complimentary mating features to those on the sonication plate. A method for sonication of multiple samples includes utilizing mating features to attach tubes to the sonication plate and energizing the sonicator to vibrate the sonication plate. The invention also relates to arrangements for continuous flow-through useful for sonicating large sample volumes. For continuous sonication, a method is provided wherein flow-through mating connectors are attached to mating features on the sonication plate. Tubing is attached to one side of the mating connectors as input from a sample reservoir, while other tubing is attached to other side of mating connectors as output to collection vessel(s).

BRIEF DESCRIPTION OF THE DRAWINGS

Attention is now directed to several drawings that illustrate features of the present invention.

Several drawings and illustrations have been presented to aid in understanding the present invention. The scope of the present invention is not limited to what is shown in the figures.

DETAILED DESCRIPTION AND PREFERRED EMBODIMENTS

The present invention relates to sonication devices (sonicators) with optimized coupling of a vibrating element to sample containers or fluid conduits. In particular, the invention relates to non-invasive sample containers that mate with a plate sonicator at the specified insertion locations, in order to maximize coupling and produce optimal mechanical energy transfer.

Figure 1:
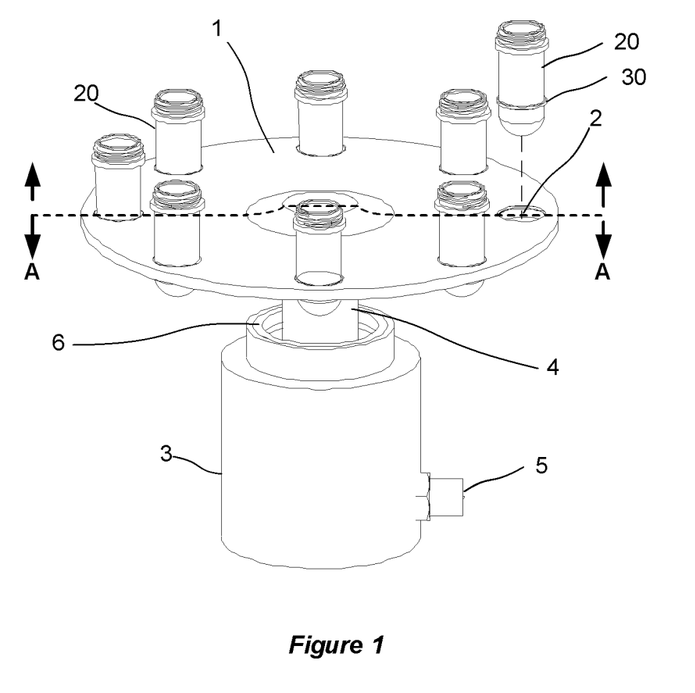
FIG. 1 is an elevated view of the sonication device and tubes.
Figure 2:
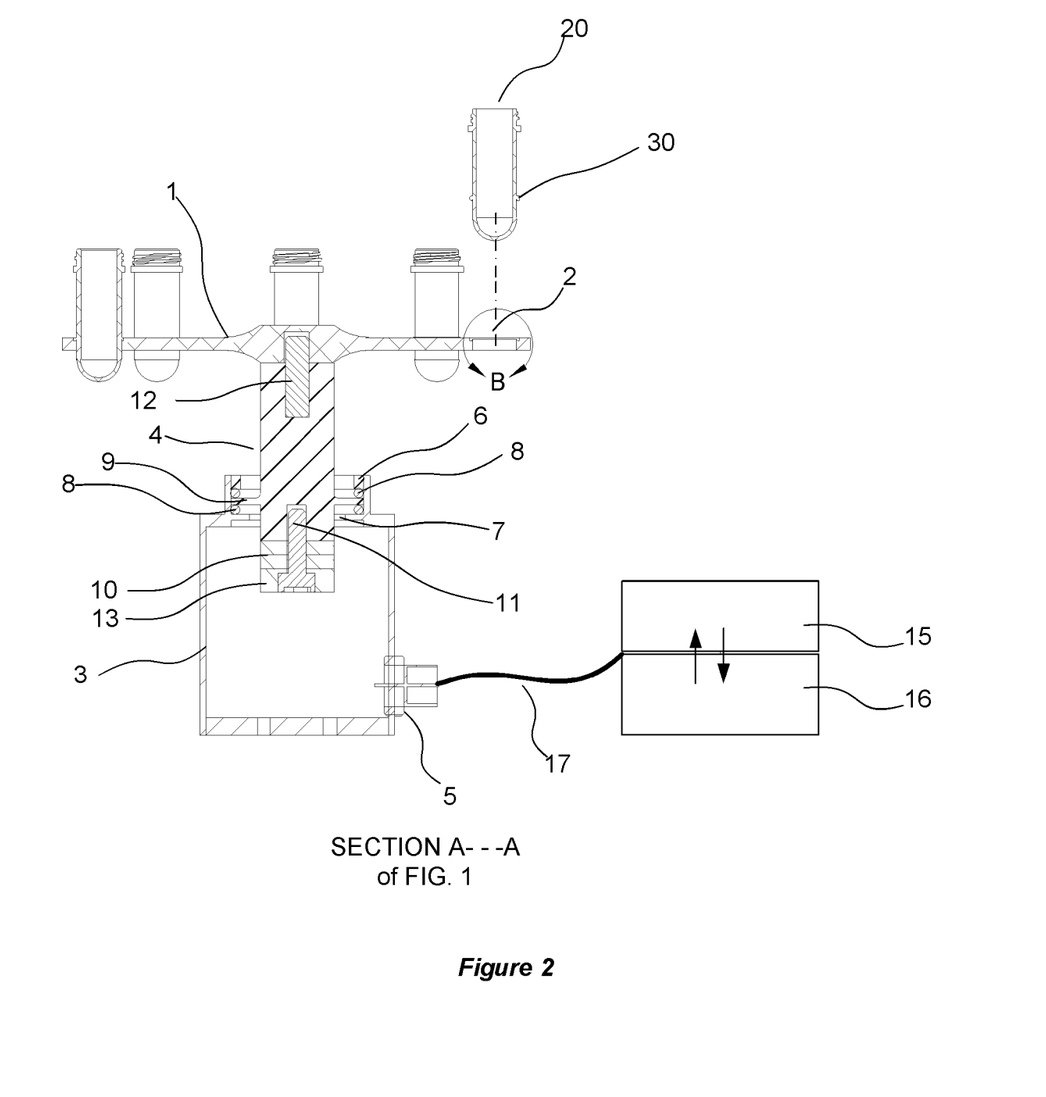
FIG. 2 is a cross-sectional view along the A - - - A line marked in 0.

FIG. 1 describes an elevated schematic view of the present sonicator, and FIG. 2 shows a cross sectional view of along the plane represented as A - - - A in FIG. 1. Referring to FIGS. 1 and 2, a sonication plate 1 is attached to a converter 4, which is attached to ultrasonic transducers 10.

Transducer 10 is preferably a piezoelectric ceramic, such as doped zirconium titanate. Other materials which convert electrical or magnetic energy into mechanical energy, such as magnetostrictive and piezomagnetic materials may also be used. Typically, two transducers 10 are employed in a "sandwich" configuration where one transducer is aligned on top of the other. Other arrangements of transducers can be employed with the condition that they are aligned such that the vibrational waves they emit do not destructively interfere, or cancel out each other. Depending on its geometry, converter 4 may increase (amplify) or reduce the energy density, or as presented in FIGS. 1 and 2 may leave the energy density unchanged. Converter 4 contains fastening features, such as a bolt 12, which secures the sonication plate to the amplifying horn assembly. Set screw 11 secures the ultrasonic transducers to a support disc 13. Other fastening mechanisms such as specialty adhesives, clamps, and the like may be applied.

Transducers 10, converter 4, and fastening features are contained in an enclosure 3, which has a connector 5 to communicate electrical energy to the transducers. The transducers are energized by an oscillating electrical power supply 15. Electronic and power control circuitry 16 match the mechanical and electrical impedance of the assembly and provide a microprocessor and user interface.

Converter 4 is secured to enclosure 3 with flange 9, using retaining ring 6 and ridge 7, and may be cushioned using shock absorbing rings 8. Flange 9 is preferably secured to the enclosure 3 at a node with regard the vibrational wave emitted from the piezoelectric transducer and through the convertor. The nodes are generally at $(n+\frac{1}{2})$ lambda, where n is an integer and lambda is the wavelength of the vibrational wave. On the other hand, the sonication plate 1 is preferably placed at a location with maximum vibrational amplitudes: at $(n+(m/4))$ lambda, where n is an integer (0, 1, 2, etc.) and m is either 1 or 3.

When the transducers are energized by means of an oscillating electrical power source 15, vibrational waves travel along the converter in the vertical direction in FIG. 2. The sonication plate 1, being placed transversely to the direction of the propagation of the waves emitted from the piezoelectric transducer, responds to the wave arriving from the converter with the result of the formation of transverse or "plate" waves. By transverse it is meant that the sonication plate is placed in an orientation in which its flat faces are substantially perpendicular to the direction of the propagation of the waves emitted by the transducer.

Plate waves may take different forms and modes depending on the geometry, dimensions, and material of the plate. Of particular interest are circular modes of waves that are concentric with the circular plate edge. Scattering and reflection of the waves occurs at the sonication plate edges, where the waves encounter an interface with air. Air is a medium with acoustic impedance significantly different from the sonication plate material, preferably a metal, e.g. aluminum, such as to cause wave scattering and reflection. The reflected waves form an interference pattern by interacting with the incident waves. At particular frequencies and assembly geometries, the interference patterns form "standing waves" which can be predicted from theoretical considerations. Finite element analysis (FEA) simulations can also be used to visualize the vibrations for allowable modes. In a preferred approach, experimental measurements can locate the standing waves with the aid of sand and other particulates, since the particulates form concentric circles located at the nodes (minima) of the waves. The vibrational modes and the resulting standing waves depend on the frequency, plate material and dimensions, and in general the electrical and mechanical impedance of the vibrating assembly. They may also depend upon the location of any discontinuous regions in the plate such as holes and the like.

It is important that the frequency of the electrical power supply 15 matches particular vibrational modes characteristic of the sonication plate. Of particular interest are vibrational modes that produce concentric circular vibrational modes. These modes are known in the art to be most stable in terms of uniform delivery to sample tubes.

Sonication plate 1 is preferably made of metal such as aluminum, titanium, and stainless steel, although hard plastic and composite material may be used. The sonication plate preferably contains multiplicity of attachment holes 2, to receive sample tubes 20. The attachment holes 2 are typically placed at of the maximal energy circumferences of the observed plate waves. Additionally, the attachment holes possess features that mate with specific sample tubes. It is an object of the present invention to provide tubes with features for mating with the feature in the attachment holes. This matching of the features of the plate's attachment holes and those of the tubes provides optimal acoustic energy coupling of the sample tubes and the sonication plate for efficient energy transfer to the tubes. Poor acoustic coupling leads to loss of energy, for example, the presence of air gaps in the interface between the plate attachment holes and the sample tube would lead to inefficient acoustic coupling and energy delivery to the sample. It is for this purpose that the sample tubes possess attachment features which mate with the attachment holes features in the sonication plate. The standing wave pattern on the plate can be affected by discontinuities in the plate such as holes or sample tubes since each can cause unwanted reflections of the wave. This can be avoided or partially avoided by designing the sample tube inserts to match the impedance of the plate as closely as possible. Also, impedance matching causes maximal transfer of energy into the sampling tube.

An advantage of the matching features just described is that, in addition to energy efficiency, the present invention provides reproducible attachment of tubes, and the ease of use in their placement and removal. The mating features include, but are not limited to, threads, snaps, such as annular snap, bayonet hooks, etc., to ensure mating of the sample tube 20 to the sonication plate attachment holes 2.

FIGS. 3A-3B illustrate a sample tube 20 shown as a cross section in FIG. 2. In FIG. 3A, the sample tube 20 contains threads 21 for a cap cover (not shown) with walls 22 and attachment feature 30. Attachment feature 30 is used to attach tube to attachment holes 2 of sonication plate 1. The sample tube is preferably made of polymeric material that can be molded or machined to form sample tubes which exhibit certain flexibility and chemical compatibility with the (fluid) sample contained in said tube. Polymers such as polyolefins, and more specifically polypropylene and polyethylene, form a preferred class of polymers. Other polymers and copolymers such as polyaromatics, polyester, polyacrylamide may also be used. Any type of sampling tube made of any rigid or semi-rigid material is within the scope of the present invention.

Figure 3:
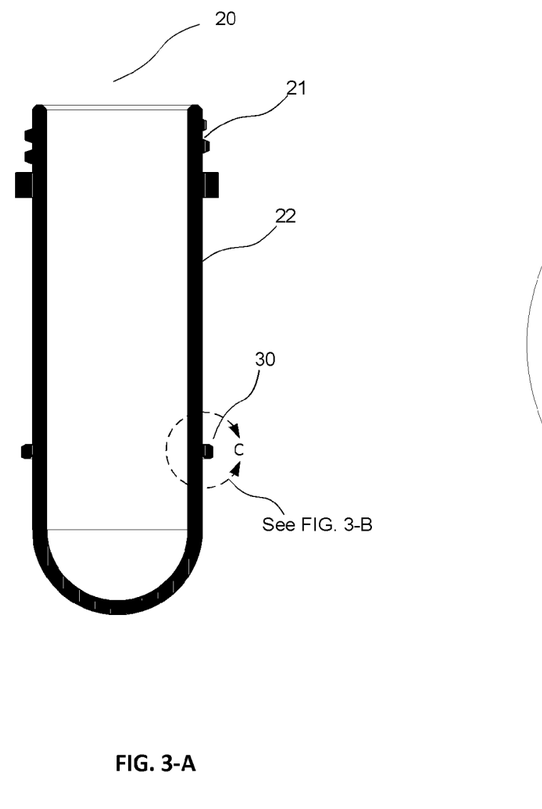
FIGS. 3A-3B show a sample tube, which is a detailed view (FIG. 3-A) of the tube 20 in FIG. 1. and showing attachment features, further detailed in FIG. 3-B.

A tube attachment feature in FIG. 3A (Detail C) is further enlarged in FIG. 3-B. Attachment feature 30 is an annular snap ring designed to attach to the sonication plate attachment hole 2 shown in FIGS. 1, 2, and detailed in FIG. 4. In FIG. 3B the annular snap ring has an interference portion, or undercut, 31 that is engaged by a mating groove on the sonicator plate attachment holes, as shown in FIG. 4. The annular snap fit is characterized by entry or engagement angle 32, and retaining, or release angle 33 in addition to the interference portion 31. The dimensions of the interference portion and the magnitude of the angles 32 and 33 are dictated by the elasticity of the sample tube material. The dimensions of the interference portion and the angles above, along with the elasticity of the sample tube material determine the force required to insert and remove the sample tubes. It is preferable that the entry angle 32 be between 20 and 30 degrees to facilitate tube placement i.e., make optimal the force required for the insertion and detachment of the sample tube into the attachment hole 2 of the plate. The release angle is preferred to be less than 90 degrees and preferably between 35 and 50 degrees to facilitate the removal of the sample tube. The force required to insert and remove the sample tube is achievable using the annular snap fit just described because the sample tube is preferably made from deformable polymers, and is filled with fluids: liquid and air.

Figure 4A:
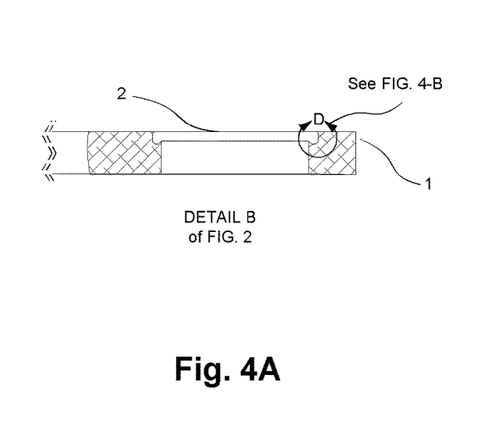
FIGS. 4A-4B show a detailed view of the attachment hole in sonication plate (FIG. 4-A), and further detailed in FIG. 4-B.
Figure 4B:
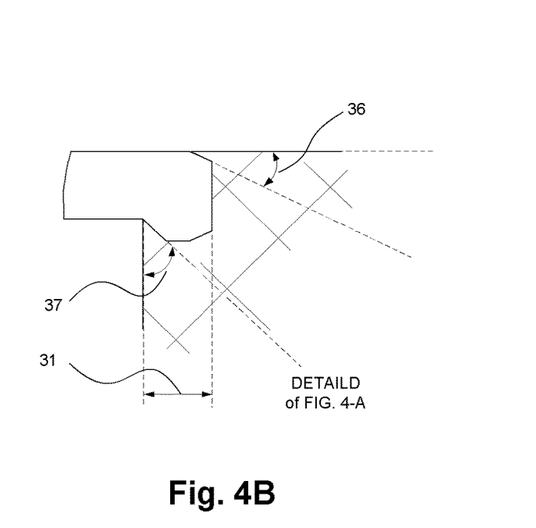

FIG. 4-A shows an enlargement (detail B in FIG. 2), additionally detailed in FIG. 4-B, of the mating hole in the sonication plate and showing a complimentary annular snap fit groove to the annular snap fit feature of the sample tube, described in FIG. 3. The dimensions of and profile of the groove match those in the annular snap fit in FIG. 3, where angle 36 equals angle 32, and angle 37 equals angle 33.

Figure 5:
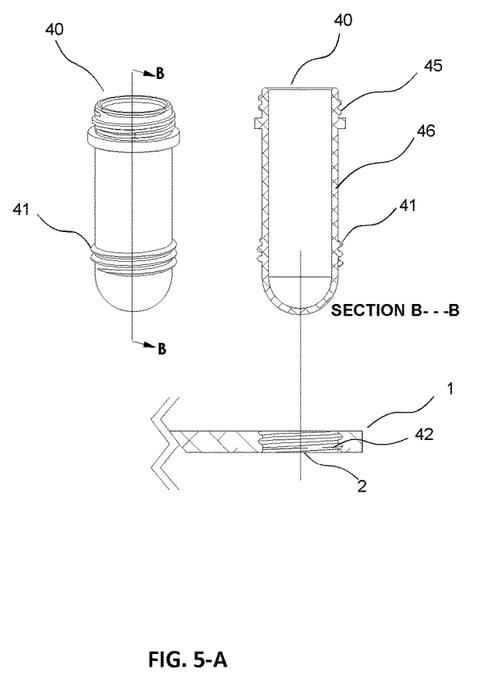
FIGS. 5A-5B show a sample tube with different attachment features (FIGS. 5-A and 5-B).

The annular snap feature just described represents a preferred embodiment of attaching the sample tube to the sonication plate. The profile shown in FIGS. 3A-3B may be of different shapes, such as hemispherical profiles. Attachment embodiments may include threads shown in FIG. 5A and a combination of threads and an annular snap fit shown in FIG. 5B. Referring to FIG. 5A, sample tube 40 is represented with an elevated view on the left and a cross section on the right. Sample tube 40 possesses thread 41. Matching threads 42 are profiled in the sonication plate 1. Similarly, in FIG. 5B, a combination of an annular snap fit 52 and a thread 51 is shown.

Figure 6:
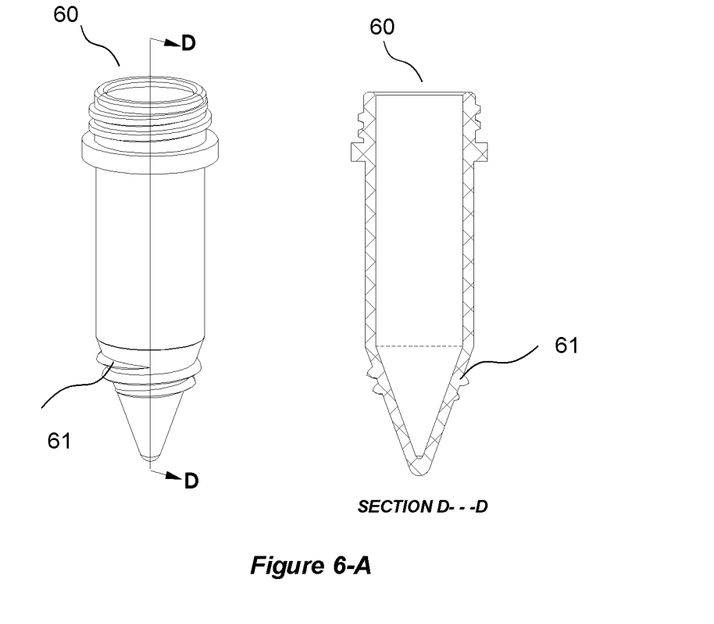
FIGS. 6A-6B show a sample tube with additional attachment features (FIGS. 6-A and 6-B).

In the case where sample volumes are small, e.g., diagnostic human samples, the sample tube may be modified to accommodate small volumes. A preferred embodiment is presented in FIGS. 6A-6B, where the bottom of the sample tube 60 is conically tapered to allow the sonication and retrieval of small sample volumes. The conical taper in FIG. 6A contains attachment features to ensure communication of the sonication power to the sample. In FIG. 6A, sample tube 60, shown with an elevated view on the left and cross section on the right, contains a conical shaped bottom which contains a thread 61. FIG. 6B shows sample tube 70 with an annular snap fit 71. Matching features are profiled in the sonication plate similar to those described in FIGS. 1-5. Other attachment features for the sample tube include, but are not limited to, press fit, bayonet snaps, and cantilever hooks.

It is an object of this invention to provide sonication plate/sample tube combinations that offer efficient energy transfer, non-invasive and easy handling of sample tubes loading and unloading. A preferred embodiment of such combinations includes a sonication plate with attachment holes that contain features complementing similar features on sample tubes.

Preferred embodiments of complementing similar features of the sonicator plate and sample tubes include threads, snaps, hooks and press fit; and preferably helical vanishing threads, annular snap rings, and bayonet hooks.

A method of sonicating samples using the present invention is achieved by attaching at least one sample tube possessing an attachment feature to matching attachment features of the sonication plate attachment hole; energizing the transducers by providing electrical energy to the transducer which in turn is transferred to vibrational energy and is communicated to the sonication plate to form standing sonic waves across the sonication plate. A sample in the sample tube is therefore subjected to the energy of the standing sonic wave further subjecting the constituents present in the sample to sonication. Samples that may be sonicated may be any sample containing material intended to be affected by sonication. Biological samples include, but are not limited to, human and animal body fluids such as blood, serum, plasma, cerebrospinal fluid, urine, lymph fluids, ascites fluid, tears, saliva, sputum, milk and the like, as well as biological fluids such as cell culture supernatants.

It is an object of the present invention to provide sonication using continuous flow arrangements. Such arrangements provide key advantages in terms of applicability to large volumes, lower power utilization and, and non-invasive handling of the sample volume.

It is another object of the present invention to provide apparatus and methods of sonicating large volume of fluid samples containing biological organisms for the purpose of extracting useful biological compounds from said organisms.

Figure 7:
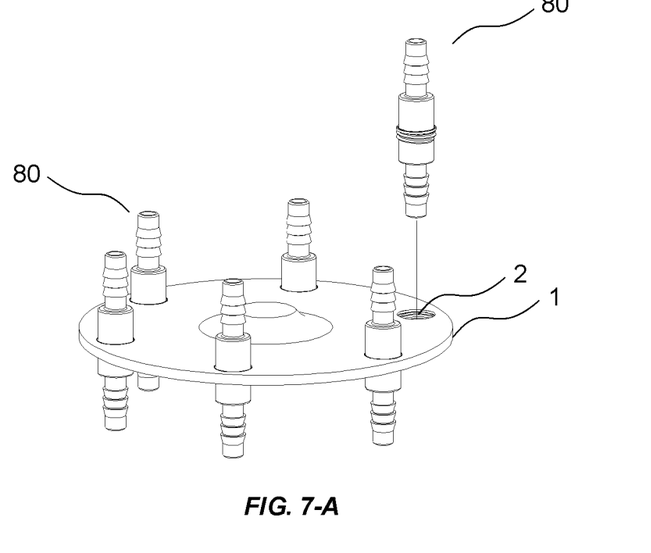
FIGS. 7A-7C show a sonication plate with fluidic connectors (FIG. 7-A), with details of the fluid connector (FIG. 7-B), and with the fluid connector's cross section in FIG. 7-C.

FIG. 7A shows a preferred embodiment of sonication plate arrangement for continuous sonication of a large sample volume. In FIG. 7A, six fluidic connectors 80 are illustrated with the sonication plate 1; the rest of the sonication device components is similar to those in FIGS. 1-2, and are not shown in order to simplify the drawings. Different numbers of holes and fluidic links may be used to accommodate specific applications depending on the fluid type ad volume to be processed. FIG. 7B shows an elevated view of fluidic connector 80 with attachment features 81 similar to those discussed above for sample tubes, e.g., annular snap fits, threads, etc., or combination thereof. Fluidic connector 80 is fitted into holes 2 of sonication plate 1 with matching features. Fluidic connector 80 acts as a flow-through sonication/lysis chamber. Fluidic connector 80 is preferably made of plastic, e.g., polyolefins and other materials similar to those enumerated for the sample tube, 20. Any rigid or semi-rigid material is within the scope of the present invention.

FIG. 7C is a cross section through fluidic connector 80 in FIG. 7B, and represents a preferred embodiment of the connector. In FIG. 7C, fluidic connector 80 is shown with a porous filter element, or a mesh, 84 to support the inclusion of particulate matter, e.g., glass beads 83. The particulate matter is preferably resistant to the sonication energy in the range usually applied in biological lysis by sonication. Filter element 84 is preferably made of chemically inert, biologically compatible porous material such as plastic, ceramic, or metal. The porosity of filter element 84 is preferably chosen to be smaller than the diameter of the glass beads, but larger than the largest particulate matter sonicated in the fluid stream. For example, if the largest particulate matter in the sonicated fluid stream is 100 microns, the filter's pore size should be larger than 0.1 mm, preferably between 0.15 and 5 mm, and the glass beads' diameter to be used should be larger than the largest pore diameter in the filter, preferably 1.1 to 5 times the largest pore diameter of the filter. Particulate matter is preferably glass beads, but may also be of metals, e.g., stainless steel, or other non-reactive durable metals and ceramic. Glass beads are known to enhance the sonication efficiency and disturbance of the fluid medium during sonication. Glass beads may be of diameter between 0.5 microns and 50000 microns, and preferably between 1 micron and 500 microns.

Figure 8:
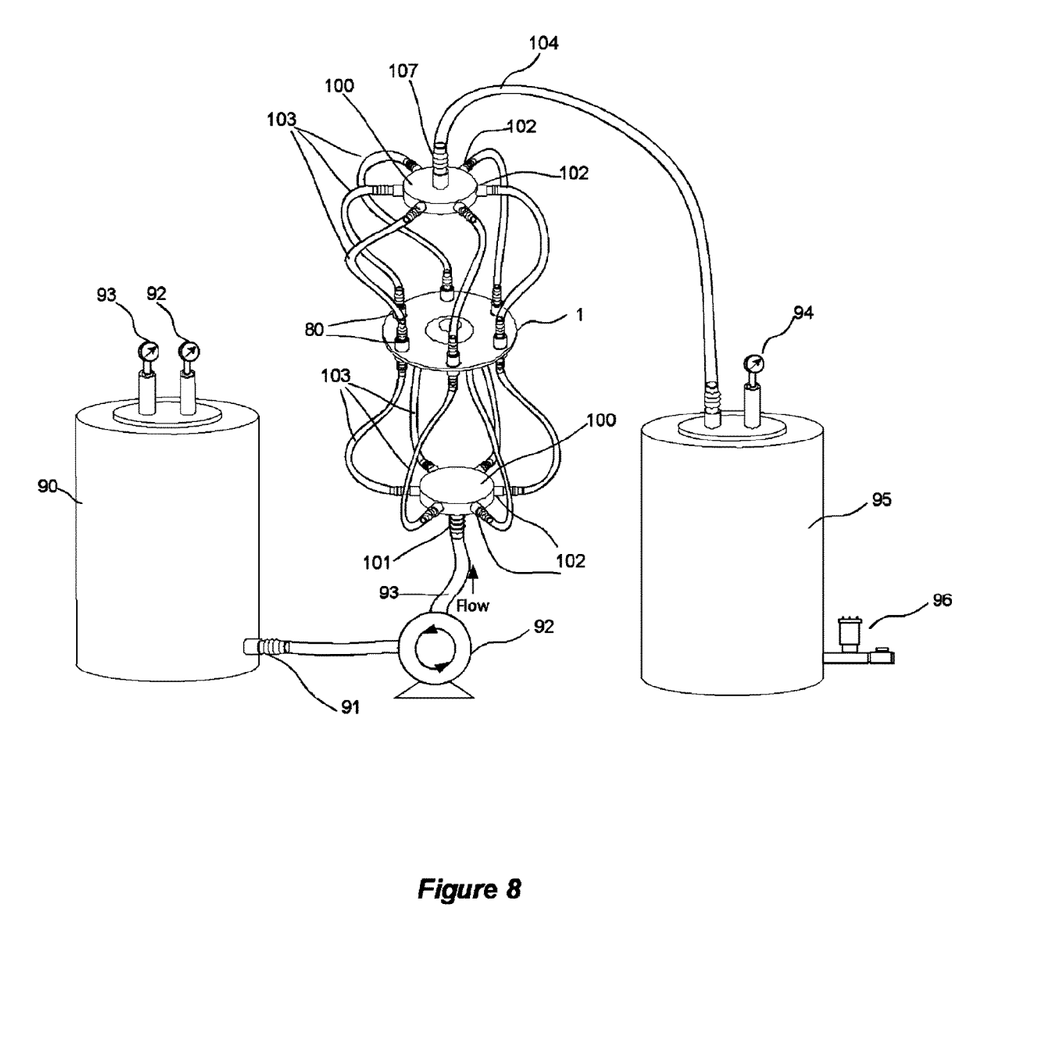
FIG. 8 is an assembly of a continuous flow sonication device

FIG. 8 shows an assembly for sonication of a large sample volume. Input fluid is contained in source vessel 90, and exits through port 91 into pump 92. Pump 92 delivers input fluid to be sonicated to inlet port 101 of multiport valve 100 by tubing 93. Multiport valve 100 divides the fluid input into outlet ports 102 which are connected through tubing 103 to fluidic connectors 80. Fluid connectors 80 which are described above and detailed in FIG. 7B and FIG. 7C, mate intimately with attachment features in sonication plate 1 as described above. Sonicated sample exits fluidic connectors 80 and enters multiport valve 110 which combines input streams into a single output stream through port 107 to enter the collection vessel 95 though tubing 104. The sample may be continuously collected through exit port 96. Source vessel 90 and collection vessel 95 may contain process control and process indicator devices 92, 93, 94, for control and detection of e.g. fluid level, temperature, pressure, etc.

Pump 92 controls the flow rate of the fluid to be sonicated, i.e., sonication time. Fluid flow rate depends on sonication power, number of samples on plate, degree of sonication desired, and input sample characteristics, such as viscosity, density and constituents. Flow rates determine the sonication time or 'residence time' in the sonication zone. This time can be calculated from flow rates and geometry of the fluidic connectors. Residence time can be in the order of fractions of a second to minutes, e.g., between 0.1 seconds and 30 minutes, and preferably between 1 second and 5 minutes. The applied sonication power per unit volume may be in the range of 0.01 watt/ml to 100 watt/ml, and preferably between 0.1 and 10 watt/ml. The applied energy depends on the configuration of the sonication device, i.e., batch mode vs. continuous flow; flow rate, the fluid characteristics and other factors as mentioned above for flow rates.

Other preferred flow arrangements include gravity flow by placing the sonicator lower than the source vessel. The flow rate in this case can be controlled by the height difference and by the use of fluidic valves.

A method of sonication a large sample volume according to the present invention, and referring to FIG. 8, includes providing an input fluid at specified flow rates; dividing the input fluid into multiple streams; delivering the divided input streams to connectors 80 which are intimately mated to sonication plate 1; energizing the sonication plate using the sonication device in FIGS. 1 and 2 with power sufficient to lyse the organisms of interest at the specified flow rates; optionally combining the input fluid streams after sonication; and, collecting the sonicated fluid into collection vessel (s).

An important object of the present invention is to apply the method of continuous sonication of a large sample volume wherein the sample volume contains algae. Certain types of algae have been targeted as a source of oil. Oil content of particular algae has been estimated to constitute a substantial percentage of the algae biomass. Referring again to FIG. 8, input fluid from e.g., an algae pond, is fed to fluidic connectors 80 at specified flow rates after dividing the input fluid into multiple streams. Connectors 80 are intimately mated to sonication plate 1. When energized, the sonication plate delivers energy to lyse the algae. The sonicated fluid containing the oil is collected in a holding collection vessel where further separation steps may be performed to purify the oil.

The lysis of algae according to the devices and methods of this invention allows an economical approach to the release of oil from algae. Oil from algae has been researched as alternative to fossil fuel; so called biodiesel.

The present invention may also find applications in several areas where large scale lysis of microorganisms is required such as in fermentation, biotechnology, drug manufacturing and extraction using monoclonal technologies. In all these areas, large volumes of microorganisms are grown under controlled conditions to produce a particular analyte, e.g., a protein, a drug, carbohydrates or hormones. The present invention allows efficient, cost effective enhancements. For example, in biotechnology monoclonal applications, a gene is inserted into an organism (e.g., e-coli), for the purpose of producing a specific product or a drug. After growth, the product must be released from the host microorganism by lysis. According to the present invention, as in FIG. 8, the growth medium containing the microorganisms is delivered at specified flow rates to connectors 80. When the sonication plate is energized, microorganisms are lysed to release their constituents, and are collected into collection vessels for further purification/processing. The present invention provides advantages with respect to large scale applications over commonly practiced technologies, such as the use of chemical lysis (strong alkalis, acids, and chaotropes) and mechanical shakers Organisms that can be subjected to lysis according to the present invention include suspended biomass of mammalian cells, hybridoma cells, plant cells, bacterial cells, yeast cells, insect cells, algae, and viruses.

Several descriptions and illustrations have been presented to aid in understanding the present invention. One with skill in the art will realize that numerous changes and variations may be made without departing from the spirit of the invention. Each of these changes and variations is within the scope of the present invention.

I claim:

1. A sonication device comprising:
   at least one removably attached flow-through fluidic connector constructed to provide a continuous pass-through of fluid, wherein said continuous pass-through originates at a sample reservoir and terminates at a receiving reservoir;
   a sonication plate mechanically coupled directly to a source of vibrational energy, the sonication plate containing an opening having inner walls, said inner walls including an inner mating surface articulated with one or more coupling surfaces, said opening receiving and holding the fluidic connector, the fluidic connector including one or more outer mating surfaces complementary to the one or more coupling surfaces on the inner mating surface, the sonication plate and the fluidic connector constructed such that when the fluidic connector is mated to said opening, maximal vibrational energy transfer occurs from the sonication plate into the fluidic connector.

2. The sonication device of claim 1 wherein said sonication plate is adapted to receive and hold a plurality of fluidic connectors.

3. The sonication device of claim 1 further comprising a delivery system that delivers a continuous flow of fluid through said fluidic connector.

4. The sonication device of claim 1 wherein said sample reservoir contains suspended biomass and said receiving reservoir collects fluid containing a product from said biomass.

5. The sonication device of claim 4 wherein said suspended biomass contains at least one of mammalian cells, hybridoma cells, plant cells, bacterial cells, yeast cells, insect cells, algae, and viruses.

6. The sonication device of claim 4 wherein said product is at least one of protein, hormone, vaccine, enzyme, oil, and polysaccharide.

7. The sonication device of claim 1 wherein said fluid connector contains a porous filter element, and wherein particulate matter is supported on said filter element.

8. The sonication device of claim 7 wherein said porous filter contains pores of diameter larger than the diameter of the largest particulate matter sonicated.

9. The sonication device of claim 7 wherein said particulate matter is of diameter larger than the diameter of the pores of porous filter element.

10. The sonication device of claim 7 wherein said particulate matter is of diameter between 0.5 millimeters and 50 millimeters.

11. The sonication device of claim 7 wherein said particulate matter is one of glass, stainless steel, and ceramic particulates.

12. A sonication device comprising:
   at least one removably attached flow-through fluidic connector constructed to provide a continuous pass-through of fluid, wherein said continuous pass-through originates at a sample reservoir and terminates at a receiving reservoir;
   a sonication plate mechanically coupled directly to a source of vibrational energy, the sonication plate containing an opening having inner walls, said inner walls including an inner mating surface articulated with one or more coupling surfaces, said opening receiving and holding the fluidic connector, the fluidic connector including one or more outer mating surfaces complementary to the one or more coupling surfaces on the inner mating surface, the sonication plate and the fluidic connector constructed such that when the fluidic connector is mated to said opening, maximal vibrational energy transfer occurs from the sonication plate into the fluidic connector,
   a delivery system adapted to deliver a continuous flow of fluid through said fluidic connector.

13. The sonication device of claim 12 wherein said sonication plate is adapted to receive and hold a plurality of fluidic connectors.

14. The sonication device of claim 12 wherein said fluid connector contains a porous filter element, and wherein particulate matter is supported on said filter element.

15. The sonication device of claim 1, wherein the opening is located at a region of the sonication plate adjacent to a maximal energy peak of a plate wave propagated by the sonication plate.

* * * * *